United States Patent [19]
Okamura et al.

[11] Patent Number: 5,752,514
[45] Date of Patent: May 19, 1998

[54] BIOMAGNETISM MEASURING METHOD AND APPARATUS

[75] Inventors: Shoichi Okamura, Otsu; Akira Arakawa, Ukyo-ku; Shigeki Kajihara, Uji, all of Japan

[73] Assignee: Shimadzu Corporation, Kyoto, Japan

[21] Appl. No.: 698,080

[22] Filed: Aug. 15, 1996

[30] Foreign Application Priority Data

Aug. 31, 1995 [JP] Japan .................. 7-223853

[51] Int. Cl.$^6$ .................................................. A61B 5/05
[52] U.S. Cl. .................. 128/653.1; 324/244; 324/248; 324/260; 128/731
[58] Field of Search .................. 128/653.1, 733, 128/731, 898; 324/246, 248, 244, 260, 261, 263

[56] References Cited

U.S. PATENT DOCUMENTS

| | | | |
|---|---|---|---|
| 5,361,774 | 11/1994 | Yamazaki et al. | 128/731 |
| 5,437,276 | 8/1995 | Takada | 128/653.1 |
| 5,601,081 | 2/1997 | Tomida et al. | 128/653.1 |

FOREIGN PATENT DOCUMENTS

| | | |
|---|---|---|
| 1-503603 | 12/1989 | Japan . |
| 4-135536 | 5/1992 | Japan . |
| 8-98821 | 4/1996 | Japan . |

*Primary Examiner*—Marvin M. Lateef
*Assistant Examiner*—Eleni Mantis Mercader
*Attorney, Agent, or Firm*—Nikaido, Marmelstein, Murray & Oram LLP

[57] ABSTRACT

A biomagnetism measuring method and apparatus for determining a positional relationship of an examinee with fluxmeters in a short time. A current supply unit simultaneously supplies alternating currents of different frequencies to a plurality of oscillator coils attached to the examinee, respectively. The fluxmeters detect magnetic fields simultaneously formed by the oscillator coils supplied with the currents. Field data thereby obtained are applied through a data collecting unit to a field analyzer for frequency analysis to recognize field strengths due to the respective oscillator coils for the respective fluxmeters. The field analyzer computes positions of the oscillator coils relative to the fluxmeters from the field strengths recognized for the respective oscillator coils and known values of the currents supplied to the respective oscillator coils. Based on this positional information, information indicative of positions of bioelectric current sources measured in a separate process is displayed as superposed on an MRI image of a site of interest of the examinee.

16 Claims, 9 Drawing Sheets

BIOMAGNETISM MEASURING METHOD AND APPARATUS

BACKGROUND OF THE INVENTION

(1) Field of the Invention

This invention relates to a biomagnetism measuring method and apparatus for measuring minute magnetic fields formed by bioelectric current sources in the body of an examinee or patient, and determining the bioelectric current sources based on data of the measurement.

(2) Description of the Related Art

With the recent developments in the superconducting device technique, biomagnetism measuring apparatus utilizing high-sensitivity fluxmeters called SQUID (Superconducting Quantum Interface Device) are being implemented as one type of apparatus for use in medical diagnosis. These biomagnetism measuring apparatus are expected to be useful in elucidating the functions of the brain and in diagnosing diseases of the circulatory organs.

The biomagnetism measuring apparatus is used to deduce, from data of magnetic fields measured, and by a least square or least norm method, positions, orientations and sizes of bioelectric current sources in a coordinate system where fluxmeters serve as a reference (Jukka Sarvas "Basic mathematical and electromagnetic concepts of the biomagnetic inverse problem", Phys. Med. Biol., 1987, vol. 32, No. 1, 11-22, printed in the UK).

A magnetoencephalogram thus obtained may be combined with medical images such as MRI images obtained from a magnetic resonance imaging apparatus (MRI apparatus) or X-ray images obtained from a radiographic CT apparatus, to determine a physical position of a disease or the like in the living body. It is important to grasp positional information of bioelectric current sources in the coordinate system based on fluxmeters, and their positional relationship with the medical images.

For this purpose, magnetic field generators called probe position indicators are arranged in proper positions on the surface of the head, such as near the root of the nose or under the ears. The following methods have been proposed to determine a positional relationship between the bioelectric current sources and the examinee:

(1) S. Ahlfors et al., "MAGNETOMETER POSITION INDICATOR FOR MULTI CHANNEL MEG", Advances in Biomagnetism, edited by S. J. Williamson et al., Plenum Press, New York 693-696, 1989;

(2) Neuromag-122 Preliminary Technical Data, Aug. 1991;

(3) "Method and Apparatus for Measuring Biomagnetism" (Japanese Patent Publication (Unexamined) No. H1-503603); and (4) "Position Detector for a Biomagnetic Field Measuring Apparatus" (Japanese Patent Publication (Examined) No. H555126).

In these methods, three or more oscillator coils are pasted to the body surface of an examinee. First, a direct current is applied to the first oscillator coil. A magnetic field formed by the first oscillator coil is detected by a plurality of fluxmeters whose mutual positional relationship is known. The position of the first oscillator coil relative to the group of fluxmeters is determined from the strength of the current applied to the oscillator coil, field strengths detected by the respective fluxmeters, and the positional relationship among the fluxmeters. The operation is successively applied to the second and subsequent oscillator coils to determine positions of all of the oscillator coils, thereby to determine the position of the examinee relative to the group of fluxmeters.

However, three stages of operation are required for determining the position of each oscillator coil, which are (1) determining a proper amount of current to realize a field strength detectable by the fluxmeters, (2) supplying the determined proper current to the oscillator coil, and (3) detecting the magnetic field formed by the oscillator coil. In the conventional methods, these operations must be repeated for the number of oscillator coils pasted to the body of the examinee, and no less than several tens of seconds are consumed in determining the position of the examinee. This results in a drawback that a long examination time is required for measuring bioelectric current sources.

In particular, a proposal has been made for facilitating superposition on MRI images by using an increased number of oscillator coils (Japanese Patent Publication (Unexamined) No. H8-98821). However, such a method requires a still longer time for determining the position of the examinee.

SUMMARY OF THE INVENTION

This invention has been made having regard to the state of the art noted above, and its object is to provide a biomagnetism measuring method and apparatus for determining a positional relationship of an examinee with fluxmeters in a short time.

The above object is fulfilled, according to this invention, by a biomagnetism measuring method for measuring, with a plurality of fluxmeters, fine magnetic fields formed by bioelectric current sources in the body of an examinee, and determining at least positions of the bioelectric current sources based on field data obtained, the method comprising the steps of:

determining positions relative to the fluxmeters of a plurality of oscillator coils attached to the examinee; and measuring, with the fluxmeters, fine magnetic fields formed by bioelectric current sources in the body of an examinee, and determining positions relative to the fluxmeters of the bioelectric current sources based on field data obtained;

wherein the step of determining positions of the plurality of oscillator coils includes:

simultaneously supplying alternating currents of different frequencies to the oscillator coils attached to the examinee, respectively;

measuring, with the fluxmeters, fine magnetic fields formed by the oscillator coils supplied with the alternating currents;

analyzing frequencies of field data measured with the fluxmeters, and computing field strengths due to the oscillator coils for individual ones of the fluxmeters; and computing positions of the oscillator coils relative to the fluxmeters from the field strengths computed.

In the method according to this invention noted above, positions of the oscillator coils relative to the plurality of fluxmeters are computed by simultaneously oscillating the oscillator coils with different frequencies. Compared with the method in which the oscillator coils are oscillated successively, the method according to this invention can quickly measure the positions of the oscillator coils, i.e. positions of the examinee relative to the plurality of fluxmeters. In particular, a processing time is hardly variable even where numerous oscillator coils are used, to realize a quick and accurate measurement of bioelectric current sources. After measuring positions of the oscillator coils relative to the fluxmeters and positions of bioelectric current sources relative to the fluxmeters, the relationship between these positions enables the positions of bioelectric current sources to be identified relative to the oscillator coils or relative to the examinee.

The positions of the oscillator coils may be determined, for example, from field data obtained by simultaneously oscillating the oscillator coils only once. In order to increase the precision of measurement, the positions of the oscillator coils may be determined from averages of field data obtained by simultaneously oscillating the oscillator coils a plurality of times.

The step of analyzing frequencies of field data measured with the fluxmeters, and computing field strengths due to the oscillator coils for individual ones of the fluxmeters, may be executed to determine field strengths of frequencies corresponding to frequencies assigned to the oscillator coils as the field strengths due to the oscillator coils. It is also preferable to determine field strengths having maximum values in frequency ranges including respective frequencies assigned to the oscillator coils as the field strengths due to the oscillator coils. Then, the field strengths due to the oscillator coils may be determined with high precision even where slight variations occur with oscillating frequencies of the oscillator coils.

The step of computing positions of the oscillator coils relative to the fluxmeters from the field strengths computed, may be based on a least square method for computing positions of the oscillator coils.

The method according to this invention may further comprise the step of identifying positions of the bioelectric current sources on a medical image of a site of interest of the examinee based on the positions of the oscillator coils relative to the fluxmeters and the positions of the bioelectric current sources relative to the fluxmeters. This is useful for diagnostic and other purposes in that the positions of the bioelectric current sources are recognized on a medical image of a site of interest of the examinee. In this case, the oscillator coils are attached to positions corresponding to positions of markers attached to the site of interest before the medical image is picked up of the site of interest, the positions of the bioelectric current sources being identified on the medical image by relating the positions of the oscillator coils determined to the positions of the markers on the medical image, respectively.

In another aspect of this invention, a biomagnetism measuring apparatus is provided for measuring, with a plurality of fluxmeters, fine magnetic fields formed by bioelectric current sources in the body of an examinee, and determining at least positions of the bioelectric current sources based on field data obtained, the apparatus comprising:

a plurality of oscillator coils attachable to the examinee;

a current supply unit for outputting alternating currents of different frequencies to the oscillator coils, respectively;

a plurality of fluxmeters for measuring magnetic fields formed by the oscillator coils supplied with the alternating currents;

a field recognizer for analyzing frequencies of field data provided by the fluxmeters, and recognizing field strengths due to the oscillator coils for the fluxmeters, respectively; and a field analyzer for computing positions of the oscillator coils relative to the fluxmeters from the field strengths recognized for the oscillator coils.

In the apparatus according to this invention noted above, the current supply unit supplies alternating currents of different frequencies to the oscillator coils, respectively. The fluxmeters detect magnetic fields formed by the oscillator coils. The field recognizer carries out a frequency analysis of field data received from the fluxmeters, to recognize field strengths due to the respective oscillator coils for the respective fluxmeters. The field analyzer computes positions of the oscillator coils relative to the fluxmeters from the field strengths recognized for the respective oscillator coils.

The oscillator coils are not limited to any particular type. For example, each oscillator coil may be formed by printing metal on an insulating base or by winding a metal wire around a bobbin.

The current supply unit may, for example, include a plurality of AC sources, a plurality of amplifiers connected to the AC sources, respectively, and a controller for controlling oscillating frequencies of the AC sources and amplification degrees of the amplifiers.

Each of the fluxmeters used in this invention, preferably, includes a pickup coil and a superconducting quantum interface device connected thereto.

The apparatus according to this invention may further comprise an image storage for storing medical images of a site of interest of the examinee, the field analyzer being operable to identify the positions of the bioelectric current sources on the medical images by relating the positions of the oscillator coils computed to positions of markers on the medical images.

Preferably, a display is provided for displaying, in superposition, the medical images read from the image storage, and the positions of the bioelectric current sources identified by the field analyzer.

The apparatus according to this invention may further comprise a stimulator for applying at least one of light, sound and electric stimuli to the examinee.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DESCRIPTION OF THE PREFERRED EMBODIMENT

A preferred embodiment of this invention will be described in detail hereinafter with reference to FIGS. 1 through 9.

Figure 1:
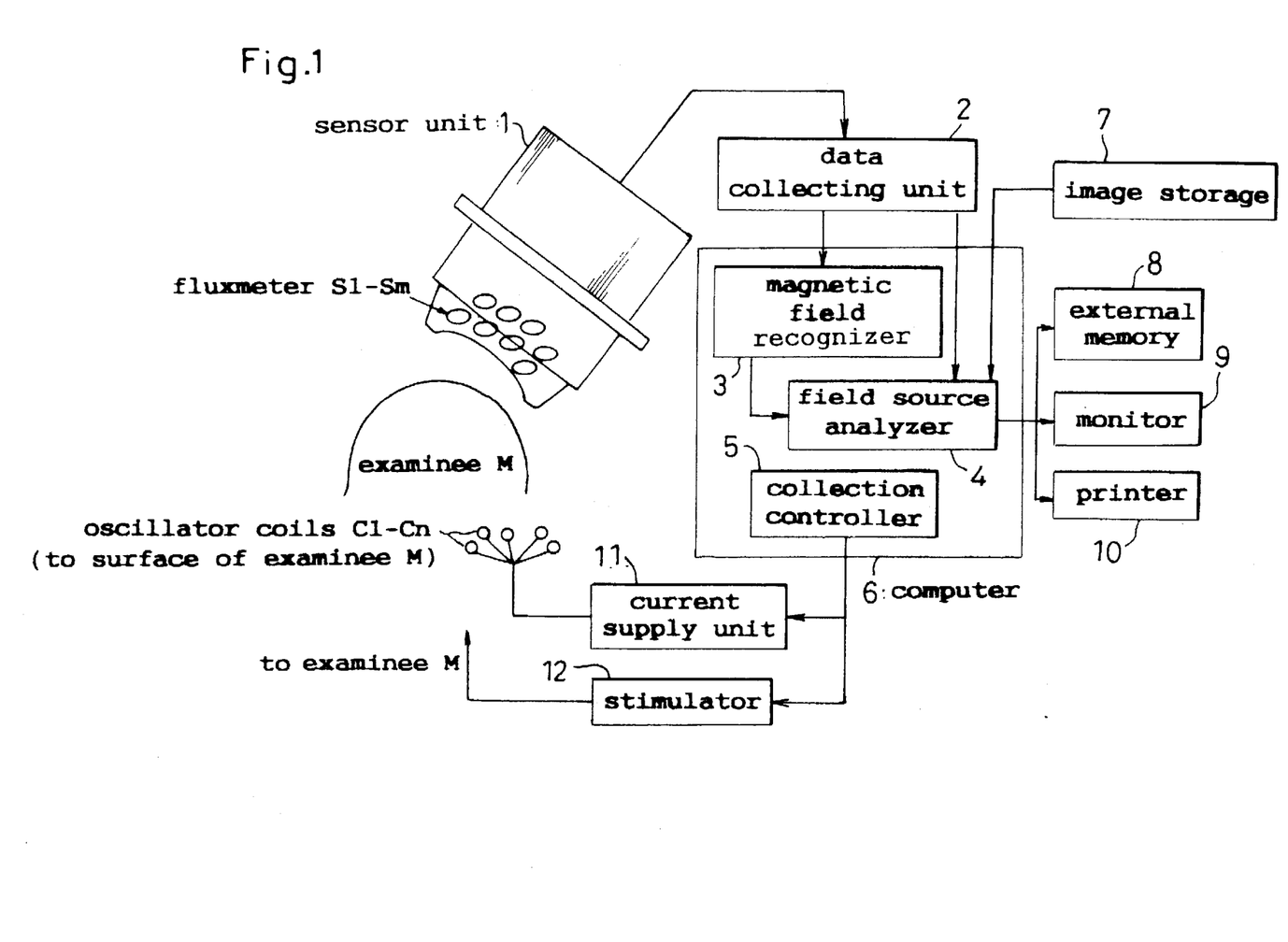
FIG. 1 is a block diagram showing an outline of a biomagnetism measuring apparatus embodying this invention.

FIG. 1 is a block diagram showing an outline of a biomagnetism measuring apparatus embodying this invention.

In FIG. 1, a sensor unit 1 includes a plurality of high-sensitivity fluxmeters S1–Sm each formed of a pickup coil and a SQUID and contained along with a coolant in a Dewar. The sensor unit 1 is placed adjacent the head of an examinee M prior to detection of bioelectric current sources.

Figure 2A:
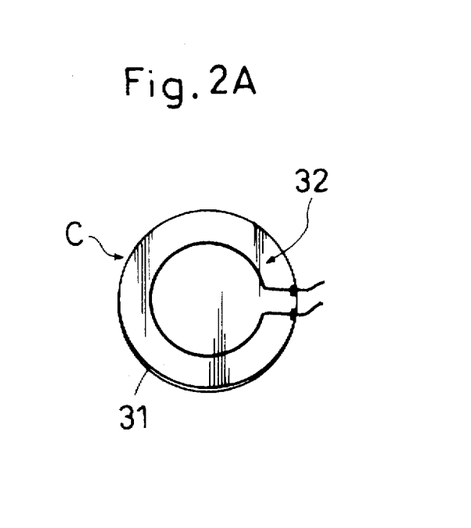
FIGS. 2A and 2B are perspective views showing examples of oscillator coils.
Figure 2B:
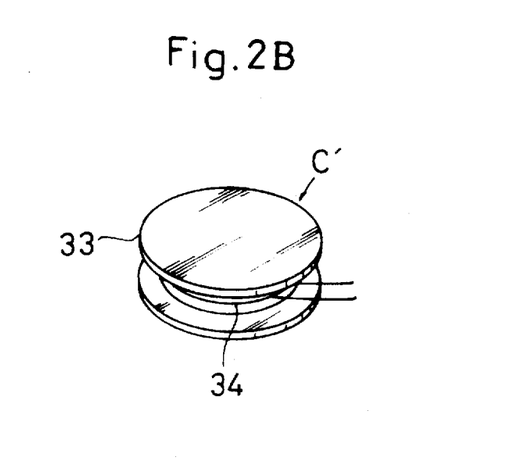

Oscillator coils C1–Cn are attached to characteristic positions for identifying the examinee M, such as near the root of the nose or under the ears. As shown in FIG. 2A, each oscillator coil C may have a base 31 formed of an insulating material such as ceramic, and a coil portion 32 formed by printing metal on the base 31. Alternatively, as shown in FIG. 2B, each oscillator coil C' may have a bobbin 33 with a metal wire 34 wound thereon.

A current supply unit 11 simultaneously outputs alternating currents of different frequencies and with individually designated strengths to the respective oscillator coils C1–Cn.

Figure 3:
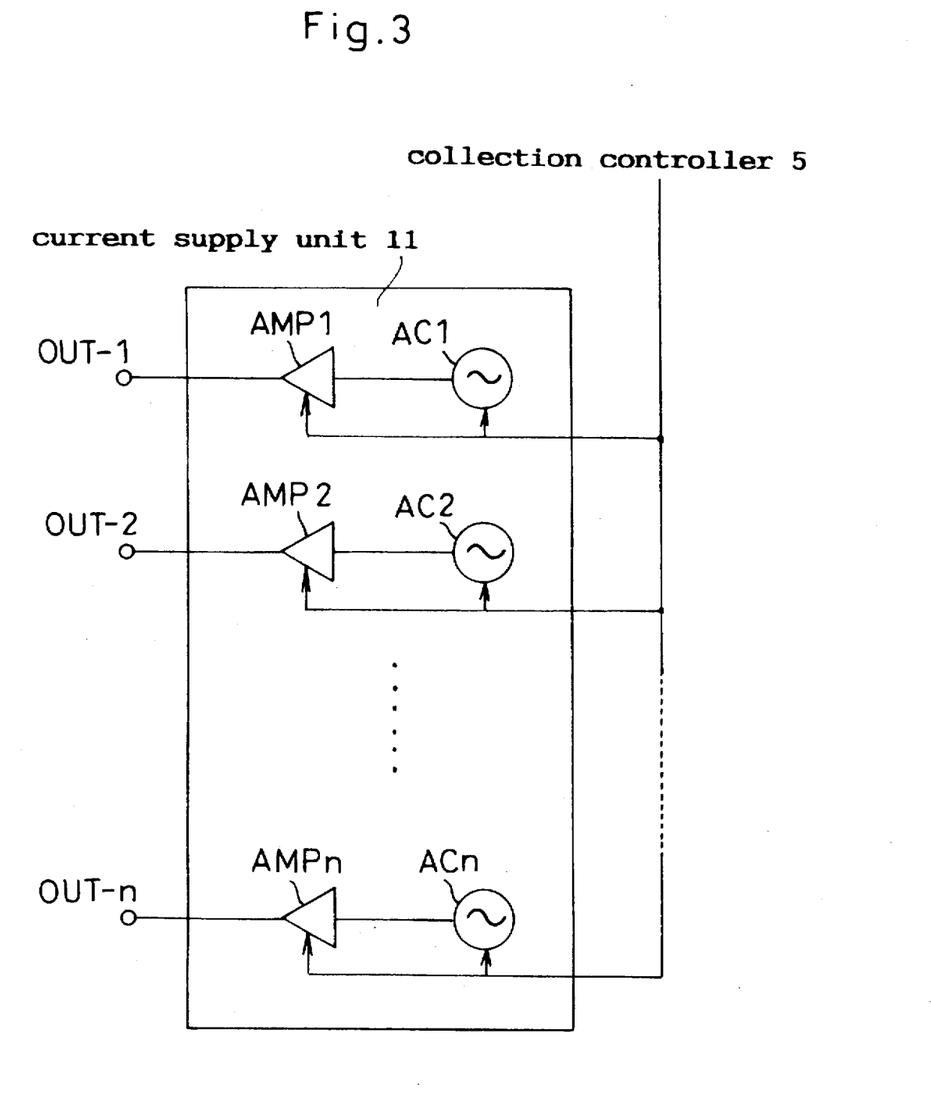
FIG. 3 is a view showing a construction of a current supply unit.

As shown in FIG. 3, the current supply unit 11 includes a plurality of AC sources AC1–ACn, amplifiers AMP1–AMPn connected to the AC sources AC1–ACn, and current output terminals out1–outn connected to the amplifiers AMP1–AMPn.

The current output terminals out1–outn are connected to the oscillator coils C1–Cn, respectively. Oscillating frequencies of the AC sources AC1–ACn and amplification degrees of the amplifiers AMP1–AMPn are individually set by a collection controller 5 included in a computer 6. The collection controller 6 also performs on-off control of the AC sources ACC1–Cn1–ACn.

A data collecting unit 2 receives AC field data produced by the oscillator coils C1-Cn and measured by the fluxmeters S1–Sm, and outputs the data after an analog-to-digital conversion to a magnetic field recognizer 3 included in the computer 6.

The computer 6 has as principal functions thereof to analyze the field data measured and to control operation of the current supply unit 11 and other components. Broadly, the computer 6 is divided into the field recognizer 3, a field source analyzer 4 and the collection controller 5.

The field recognizer 3 analyzes frequencies of the field data outputted from the data collecting unit 2, to compute field strengths individually provided by the oscillator coils C1–Cn and measured by the fluxmeters S1–Sm.

The field analyzer 4 computes positions of the oscillator coils C1–Cn relative to the fluxmeters S1–Sm, respectively, from data of the field strengths provided by the oscillator coils C1–Cn and computed by the field recognizer 3 for the respective fluxmeters S1–Sm. The positions of the oscillator coils C1–Cn computed are related to particular points near the root of the nose or under the ears of the examinee M on MRI images read from an image storage 7. Information relating to bioelectric current sources measured subsequently is displayed on a monitor 9 as superposed on the MRI images based on the positional relationship established by the field analyzer 4.

This information is stored in an external memory 8 such as an MOD (magneto-optical disk) or outputted to a printer 10 as necessary.

The collection controller 5, besides controlling the current supply from the current supply unit 11, carries out controls for instructing a stimulator 12 to stimulate the examinee 5 M with light, sound or electricity.

Figure 4:
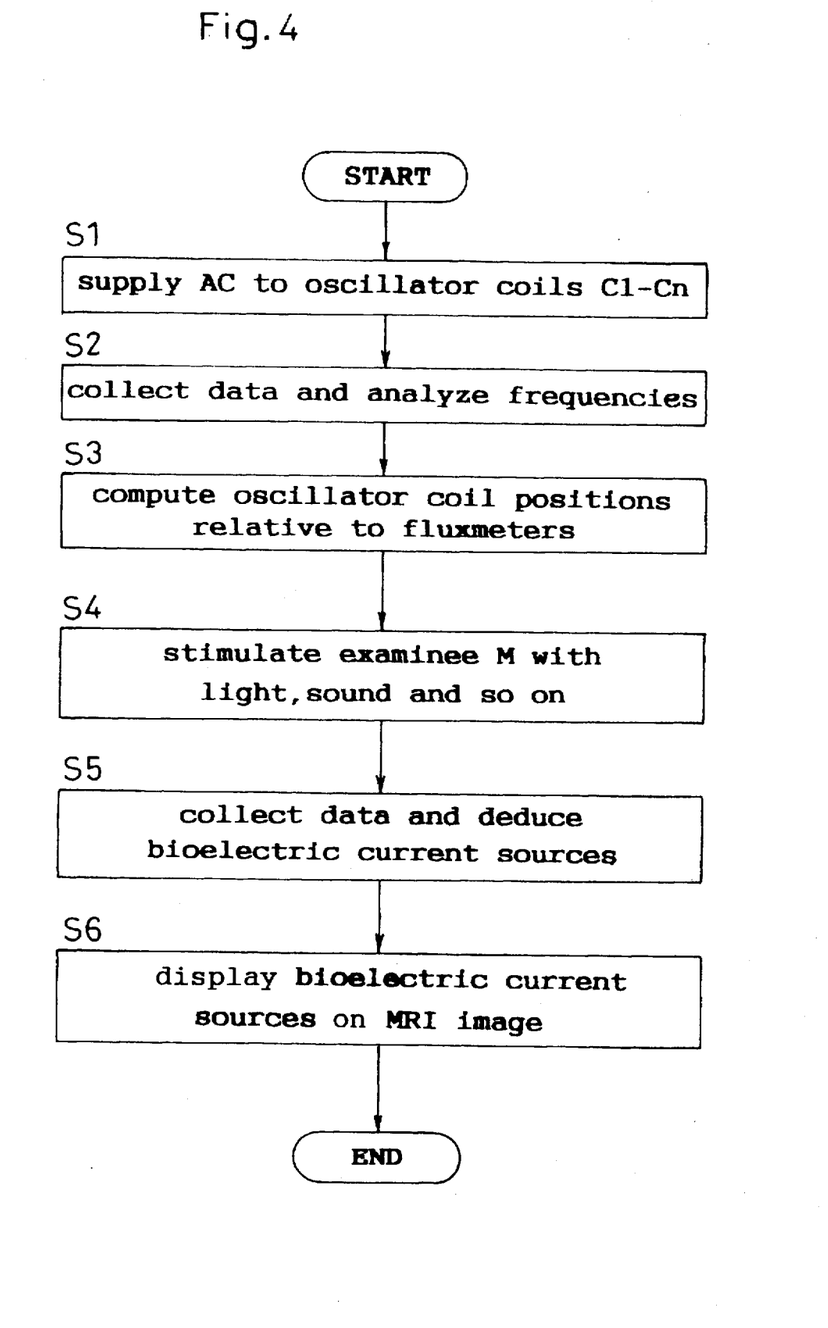
FIG. 4 is a flow chart showing an operation of the apparatus according to this invention.

Operation of this embodiment will be described with reference to FIG. 4 which is a flow chart showing an operation of the computer 6.

First, the collection controller 5 instructs the current supply unit 11 to output, simultaneously, alternating currents of different frequencies f1–fn and with individually designated strengths A1–An to the oscillator coils C1–Cn.

That is, the collection controller 5 sets oscillating frequencies and amplification degrees to the respective AC sources AC1–ACn and amplifiers AMP1–AMPn shown in FIG. 3, and instructs the AC sources AC1–ACn to output the alternating currents (step S1).

Frequency fi here has a range of setting determined by a sampling frequency in time of the analog-to-digital conversion at the data collecting unit 2. A maximum frequency fmax in the range of setting is expressed by the following equation based on a theorem of sampling:

$$fmax = fs/2$$

where fs is the sampling frequency in time of the analog-to-digital conversion.

On the other hand, the frequencies for simultaneously supplying the currents to the oscillator coils C1–Cn must have at least intervals fpitch therebetween which are expressed by the following equation:

$$fpitch = fs/Nsamp$$

where Nsamp is the number of sampling points.

For example, where 1000 samples are collected with a sampling frequency of 1 kHz, a minimum discernible frequency difference (=fpitch) between the AC sources is 1000 Hz/1000=1 Hz.

Thus, a maximum usable number of oscillator coils Nmax is expressed by the following equation:

Nmax=fmax/fpitch=Nsamp/2

Next, field data of different frequencies simultaneously produced by the oscillator coils C1–Cn are detected by the fluxmeters S1–Sm, respectively. The data collecting unit 2 performs an analog-to-digital conversion of the field data.

Then, the field recognizer 3 analyzes the frequencies, thereby measuring the field data produced by the oscillator coils C1–Cn and detected by the fluxmeters S1–Sm, respectively (step S2).

That is, the field data of different frequencies simultaneously produced by the oscillator coils C1–Cn are detected, such that one fluxmeter Sj detects the following field data Mj:

$$Mj = \sigma Bi \cdot nj$$

pwhere nj is a normal vector of the pickup coil in the fluxmeter Sj, and Bi is a field vector provided by the oscillator coil Cj in the position of the pickup coil in the fluxmeter Sj.

Figure 5:
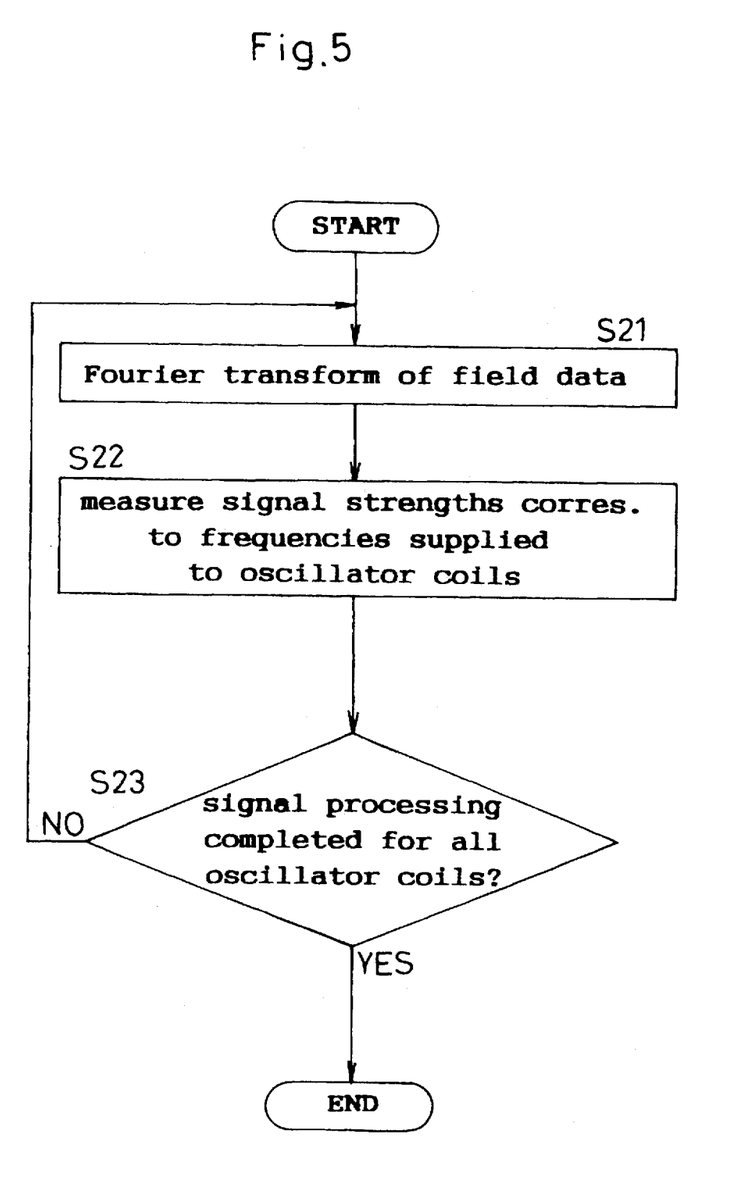
FIG. 5 is a flow chart showing an operation of a magnetic field recognizer.

A way in which the field recognizer 3 identifies detected field Mj among the fields produced by the oscillator coils C1–Cn will be described with reference to the flow chart shown in FIG. 5.

Figure 6A:
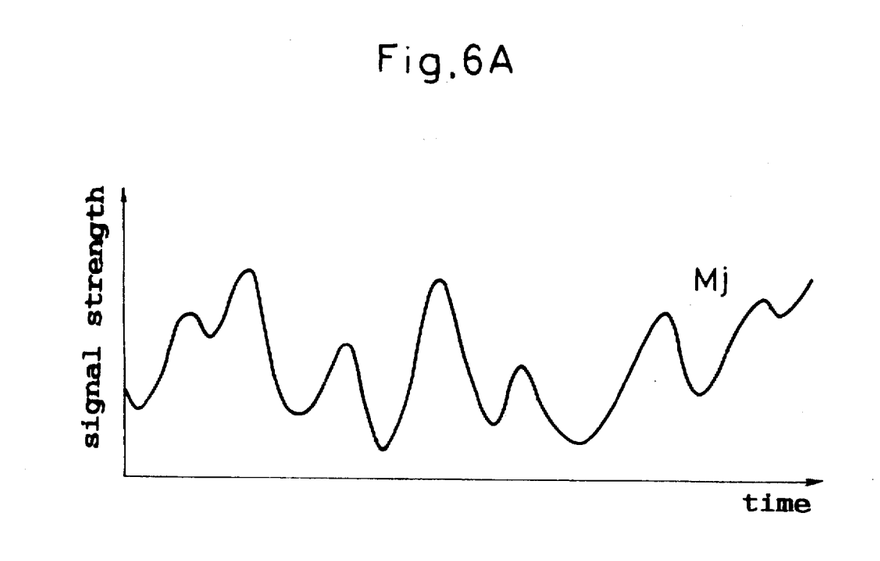
FIGS. 6A and 6B are views showing a signal detected by a fluxmeter, and frequency components of the signal resulting from a Fourier transform.
Figure 6B:
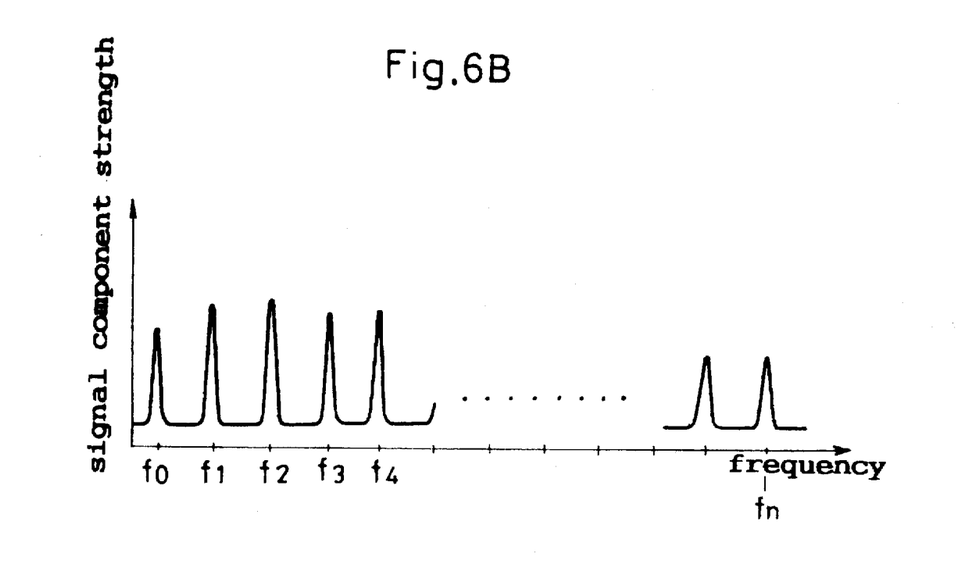

First, the field data Mj detected by the fluxmeter Sj, as shown in FIG. 6A, is put to a Fourier transform (step S21). The field data Mj detected by the fluxmeter Sj is a composite magnetic field produced by the oscillator coils C1–Cn with individual frequencies varied deliberately. Therefore, the data after the Fourier transform, as shown in FIG. 6B, provides output signals of predetermined strengths corresponding to the frequencies f1–fn of the currents supplied to the respective oscillator coils C1–Cn. Next, signal strengths Mj1–Mjn are determined for respective frequency components f1–fn, thereby to obtain field data provided by the respective oscillator coils C1–Cn (step S22).

The processes at steps S21–S22 are repeated for all of the fluxmeters S1–Sm (step S23), to obtain field data provided by the respective oscillator coils C1–Cn and detected by the respective fluxmeters S1–Sm.

Next, the field analyzer 4 computes positional relationships of the oscillator coils C1–Cn with the fluxmeters S1–Sm from the field data produced by the respective oscillator coils C1–Cn and detected by the respective fluxmeters S1–Sm and the known current strengths supplied to the oscillator coils C1–Cn (step S3).

Figure 7:
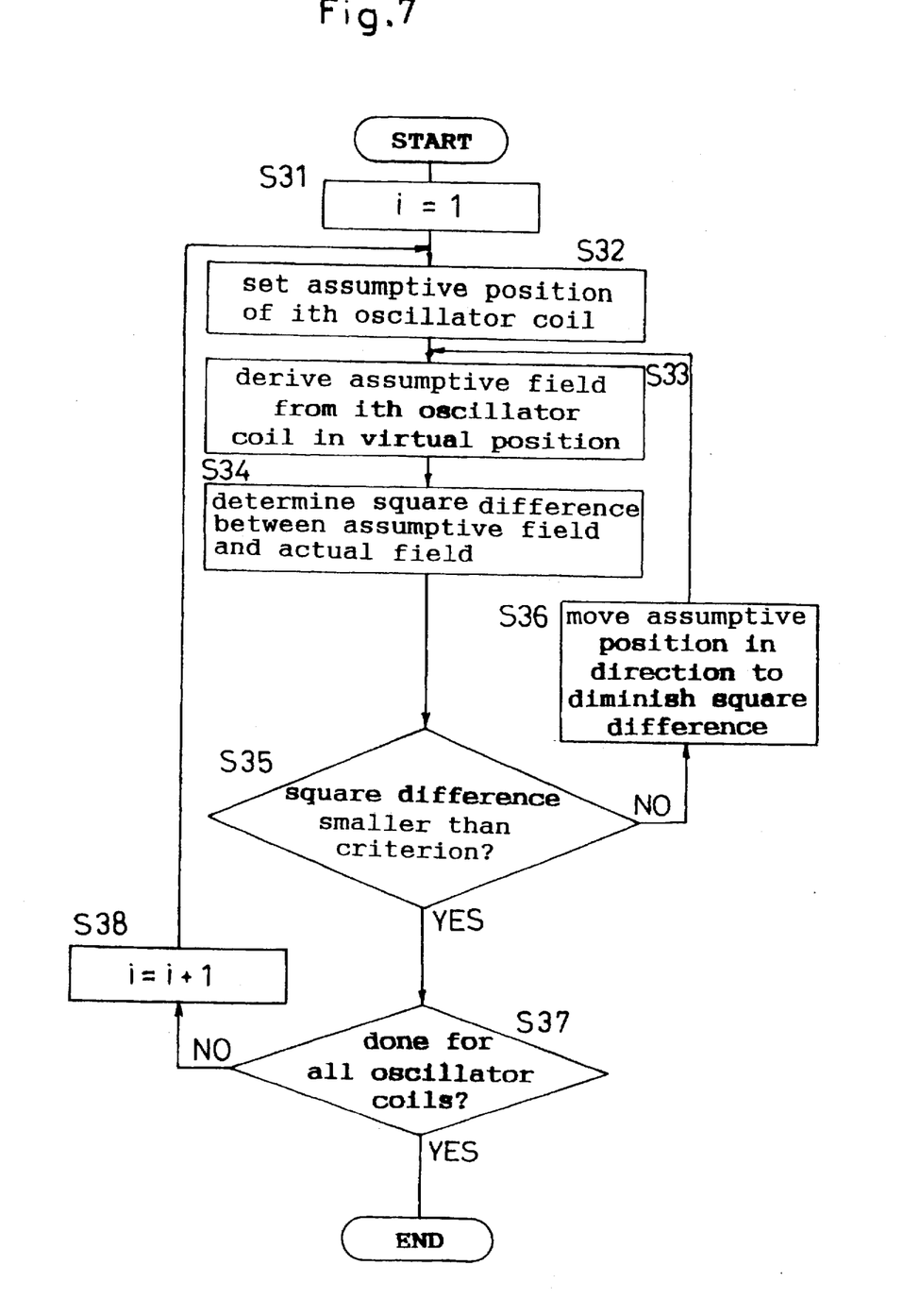
FIG. 7 is a flow chart showing an operation of a field analyzer.

A way in which the positions of the oscillator coils C1–Cn relative to the fluxmeters S1–Sm are determined will be described next with reference to the flow chart of FIG. 7 showing an operation of the field analyzer 4. In this example, the positions of the oscillator coils C1–Cn are determined by a least square method from an array of detected field strengths Mj1–Mjn assigned to the respective oscillator coils C1–Cn.

First, the field analyzer 4 uses field data produced by the first oscillator coil C1 used (step S31), and assumptively sets the position of the oscillator coil C1 (step S32). Then, the field analyzer 4 computes an array of assumptive field strengths detected by the fluxmeters S1–Sm when the oscillator coil C1 is in the assumptive position (step S33). The field analyzer 4 determines a sum of squares of differences between corresponding terms (i.e. differences between corresponding field strengths detected by the fluxmeters) in the array of assumptive field strengths and an array of actually detected field strengths Ml1–Mml. This square sum is regarded as a square difference (step S34).

Next, the square difference determined is compared with a predetermined criterion (step S35). If the square difference is larger than the predetermined criterion, the assumptive position of the oscillator coil is moved in a direction to diminish the square difference (S36). A square difference is determined for a new assumptive position thereby attained. The above operation is repeated until the square difference is less than the criterion (steps S33–S36).

If the square difference is found smaller than the predetermined criterion, the field analyzer 4 regards the assumptive position as an actual position of the oscillator coil C1, and deals with the second oscillator coil C2 (step S38). The above operation is repeated for all of the oscillator coils C1–Cn in relation to the fluxmeters S1–Sm (steps S32–S37).

Once the positions of the oscillator coils C1–Cn relative to the fluxmeters S1–Sm are determined, a required operation is carried out for measuring bioelectric current sources. That is, the stimulator 12 is operated first to stimulate the examinee M with light, sound or electricity in order to generate bioelectric currents in the body of the examinee M (step S4 in FIG. 4).

Subsequently, the fluxmeters S1–Sm detect fine magnetic fields formed by the bioelectric currents generated by the stimulus applied. Resulting data are outputted through the data collecting unit 2 to the field analyzer 4 for computing the positions of the bioelectric current sources relative to the fluxmeters S1–Sm (step S5).

Varied methods such as the least norm method and least square method have been proposed for computing positions of the bioelectric current sources relative to the fluxmeters S1–Sm. While any one of such methods may be used, a current source deducing method based on the least norm method will be described hereinafter.

Figure 8:
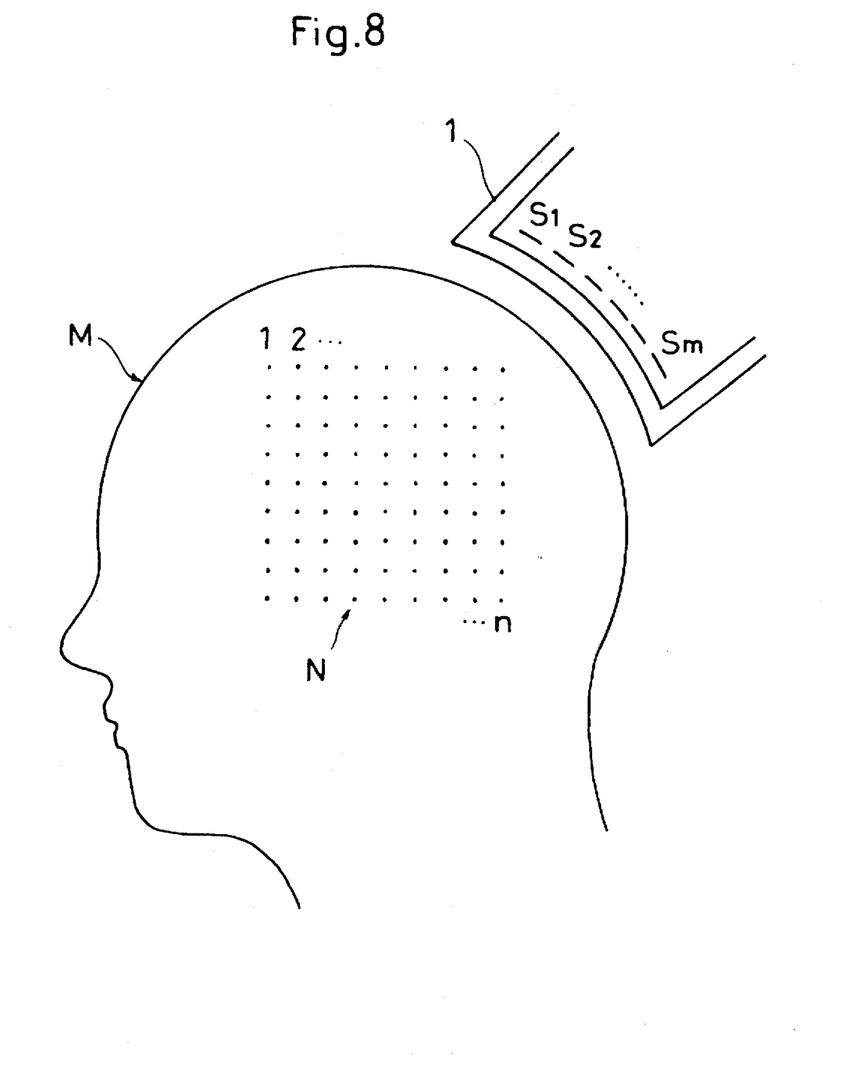
FIG. 8 is an explanatory view of a method of deducing bioelectric current sources.

As shown in FIG. 8, the sensor unit 1 is disposed adjacent the examinee M. The sensor unit 1 has fluxmeters S1–Sm arranged therein.

On the other hand, a multiplicity of lattice points 1–n are set in a region to be diagnosed, e.g. the brain, of the examinee M. Unknown current sources (current dipoles) are assumed for the respective lattice points, which are expressed by three-dimensional vectors VPj (j=1 to n). Then, the respective fluxmeters S1–Sm detect magnetic fields B1–Bm which are expressed by the following equations (1):

$$B1 = \sum_{j=1}^{n} (VPj \cdot \alpha_{1j})$$
$$B2 = \sum_{j=1}^{n} (VPj \cdot \alpha_{2j})$$
$$\vdots$$
$$Bm = \sum_{j=1}^{n} (VPj \cdot \alpha_{mj})$$

(1)

In the equations (1), $VPj=(Pjx, Pjy, Pjz)$, and $\alpha ij=(\alpha ijx, \alpha ijy, \alpha ijz)$.

$\alpha ij$ is a known coefficient representing intensity of a magnetic field detected in the position of each fluxmeter SC1–CniSm, where the current sources of unit sizes in X, Y and Z directions are arranged on the lattice points.

If $[B]=(B1, B2, \ldots Bm)$, and $[P]=(P1x, P1y, P1z, \ldots Pnx, Pny, Pnz)$, then the equations (1) are rewritten as the following linear relationship (2):

$$[B]=A\,[P] \quad (2)$$

In the equation (2), A is a matrix having 3n X m elements expressed by the following equation (3):

$$A = \begin{pmatrix} \alpha_{11x} & \alpha_{11y} & \alpha_{11z} & \cdots & \alpha_{1nx} & \alpha_{1ny} & \alpha_{1nz} \\ \cdot & & & & & & \cdot \\ \cdot & & & & & & \cdot \\ \cdot & & & & & & \cdot \\ \alpha_{m1x} & \alpha_{m1y} & \alpha_{m1z} & \cdots & \alpha_{mnx} & \alpha_{mny} & \alpha_{mnz} \end{pmatrix} \quad (3)$$

If the inverse matrix of A is expressed by $A^-$, $[P]$ is expressed by the following equation (4):

$$[P]=A^-[B] \quad (4)$$

The least norm method is based on the premise that the number of unknowns $3n$ (where the sizes in X, Y and Z directions of the current sources assumed for the respective lattice points are taken into account) is greater than the number of equations m (the number of fluxmeters S1–Sm). This method finds solutions for current sources $[P]$ by applying the condition that norm $||[P]||$ of current sources $[P]$ is minimized. The solutions could be obtained uniformly by equalizing the number of equations m and the number of unknowns $3n$, but such solutions would be very unstable. For this reason, the least norm method is employed.

By applying the condition that norm $||[P]||$ of current sources $[P]$ is minimized, the above equation (4) is rewritten as the following equation (5):

$$[P] = A^+ [B] \tag{5}$$

where $A^+$ is a general inverse matrix expressed by the following equation (6):

$$A^+ = A^t (AA^t)^{-1} \tag{6}$$

where $A^t$ is a transposed matrix of A.

The orientations and sizes of the current sources VPj on the respective lattice points are deduced by solving the above equation (5). The current source having the greatest value thereamong is regarded as the closest to a true current source.

In order to improve the position resolving power of the least norm method, least norm solutions may be gained repeatedly while subdividing the lattice points.

Figure 9:
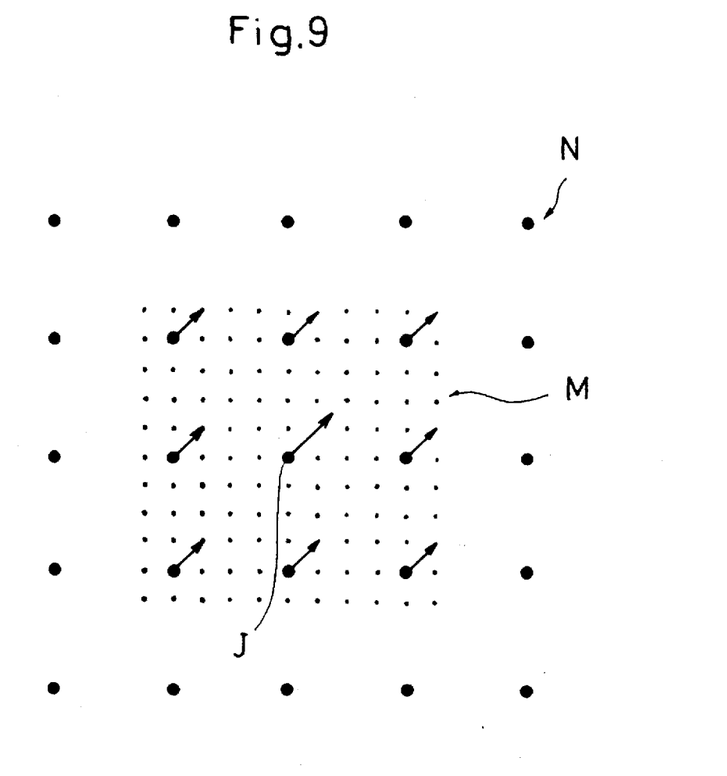
FIG. 9 is another explanatory view of the method of deducing bioelectric current sources.

FIG. 9 is an enlarged view of part of the lattice points N shown in FIG. 8. Reference J in FIG. 9 denotes the lattice point having the current source deduced by the above least norm method as being close to the true current source. A group of subdivided lattice points M (shown in small black spots in FIG. 9) is additionally established around this lattice point J. The technique described above is applied to the newly established group of lattice points M as included in the initially established group of lattice points, to deduce a current source still closer to the true current source.

After the positions of the oscillator coils C1–Cn relative to the fluxmeters S1–Sm and the positions of the bioelectric current sources relative to the fluxmeters S1–Sm are determined as described above, an MRI image picked up of the examinee M in advance is read from the image storage 7.

Information showing the bioelectric current sources is displayed on the monitor 9 as superposed on the MRI image (step S6).

A method of displaying the information showing the bioelectric current sources as superposed in a predetermined position on the MRI image will be described. First, markers for MRI image pickup are attached to positions where the oscillator coils C1–Cn are to be attached. As a result, the markers attached appear on an MRI image picked up. For measuring bioelectric current sources, the markers are removed, the oscillator coils C1–Cn are attached in place, and the positions of the oscillator coils C1–Cn are identified.

Consequently, the positions of the oscillator coils C1–Cn are determined on the MRI image by relating the positions of the oscillator coils to the positions of the markers appearing on the MRI image. In this way, positions of the bioelectric current sources are identified on the MRI image.

The above computation produces improved results if the oscillator coils have substantially circular coil portions and no variations occur among the coil portions of all the oscillator coils.

In the foregoing embodiment, positions of the oscillator coils relative to the oscillator coils are determined from field data obtained from a single oscillating operation. This invention is not limited thereto, but may use averages of field data obtained from a plurality of oscillating operations to compensate for any instability of the AC sources.

In the foregoing embodiment, signal strengths corresponding to the frequencies emitted from the respective oscillator coils are obtained from Fourier-transformed field data. A maximum signal strength within a range including frequencies assigned to the respective oscillator coils, e.g. within a range of frequencies determined by averaging frequencies assigned to oscillator coils at opposite sides, may be regarded as a detected field of an oscillator coil.

The present invention may be embodied in other specific forms without departing from the spirit or essential attributes thereof and, accordingly, reference should be made to the appended claims, rather than to the foregoing specification, as indicating the scope of the invention.

What is claimed is:

1. A biomagnetism measuring method for measuring, with a plurality of fluxmeters, fine magnetic fields formed by bioelectric current sources in the body of an examinee, and determining at least positions of said bioelectric current sources based on field data obtained, said method comprising the steps of:

determining positions relative to said fluxmeters of a plurality of oscillator coils attached to the examinee; and measuring, with said fluxmeters, fine magnetic fields formed by bioelectric current sources in the body of an examinee, and determining positions relative to said fluxmeters of said bioelectric current sources based on field data obtained;

wherein the step of determining positions of said plurality of oscillator coils includes:

simultaneously supplying alternating currents of different frequencies to said oscillator coils attached to the examinee, respectively;

measuring, with said fluxmeters, fine magnetic fields formed by said oscillator coils supplied with said alternating currents;

analyzing frequencies of field data measured with said fluxmeters, and computing field strengths due to said oscillator coils for individual ones of said fluxmeters; and computing positions of said oscillator coils relative to said fluxmeters from said field strengths computed.

2. A biomagnetism measuring method as defined in claim 1, wherein said positions of said oscillator coils are determined from field data obtained by simultaneously oscillating said oscillator coils only once.

3. A biomagnetism measuring method as defined in claim 1, wherein said positions of said oscillator coils are determined from averages of field data obtained by simultaneously oscillating said oscillator coils a plurality of times.

4. A biomagnetism measuring method as defined in claim 1, wherein the step of analyzing frequencies of field data measured with said fluxmeters, and computing field strengths due to said oscillator coils for individual ones of said fluxmeters, is executed to determine field strengths of frequencies corresponding to frequencies assigned to said oscillator coils as said field strengths due to said oscillator coils.

5. A biomagnetism measuring method as defined in claim 1, wherein the step of analyzing frequencies of field data measured with said fluxmeters, and computing field strengths due to said oscillator coils for individual ones of said fluxmeters is executed to determine field strengths having maximum values in frequency ranges including respective frequencies assigned to said oscillator coils as said field strengths due to said oscillator coils.

6. A biomagnetism measuring method as defined in claim 1, wherein the step of computing positions of said oscillator coils relative to said fluxmeters from said field strengths computed, includes the following computing steps based on a least square method:

assumptively setting a position of a first oscillator coil among said plurality of oscillator coils;

computing assumptive field strengths detected by said fluxmeters when said first oscillator coil is in the assumptive position;

computing a square difference which is a square sum of differences between corresponding terms in said assumptive field strengths and detected field strengths due to said first oscillator coil obtained by analyzing frequencies of field data actually measured by said fluxmeters;

comparing said square difference with a predetermined criterion;

moving said assumptive position of said first oscillator coil in a direction to diminish said square difference when said square difference is larger than said criterion, computing a square difference based on a new assumptive position, and repeating the above operation until said square difference is diminished below said criterion;

identifying said assumptive position as the position of said first oscillator coil when said square difference is smaller than said criterion; and assumptively setting a position of a second oscillator coil after identifying the position of said first oscillator coil, identifying a position of said second oscillator coil through a process similar to the above, and subsequently identifying positions of all remaining oscillator coils.

7. A biomagnetism measuring method as defined in claim 1, further comprising the step of identifying positions of said bioelectric current sources on a medical image of a site of interest of said examinee based on the positions of said oscillator coils relative to said fluxmeters and the positions of said bioelectric current sources relative to said fluxmeters.

8. A biomagnetism measuring method as defined in claim 7, wherein said oscillator coils are attached to positions corresponding to positions of markers attached to said site of interest before said medical image is picked up of said site of interest, said positions of said bioelectric current sources being identified on said medical image by relating said positions of said oscillator coils determined to said positions of said markers on said medical image, respectively.

9. A biomagnetism measuring apparatus for measuring, with a plurality of fluxmeters, fine magnetic fields formed by bioelectric current sources in the body of an examinee, and determining at least positions of said bioelectric current sources based on field data obtained, said apparatus comprising:

a plurality of oscillator coils attachable to said examinee;

current supply means for outputting alternating currents of different frequencies to said oscillator coils, respectively;

a plurality of fluxmeters for measuring magnetic fields formed by said oscillator coils supplied with said alternating currents;

field recognizing means for analyzing frequencies of field data provided by said fluxmeters, and recognizing field strengths due to said oscillator coils for said fluxmeters, respectively; and field analyzing means for computing positions of said oscillator coils relative to said fluxmeters from said field strengths recognized for said oscillator coils.

10. A biomagnetism measuring apparatus as defined in claim 9, wherein each of said oscillator coils is formed by printing metal on an insulating base.

11. A biomagnetism measuring apparatus as defined in claim 9, wherein each of said oscillator coils is formed by winding a metal wire around a bobbin.

12. A biomagnetism measuring apparatus as defined in claim 9, wherein said current supply means includes:

a plurality of AC sources;

a plurality of amplifiers connected to said AC sources, respectively; and control means for controlling oscillating frequencies of said AC sources and amplification degrees of said amplifiers.

13. A biomagnetism measuring apparatus as defined in claim 9, wherein each of said fluxmeters includes a pickup coil and a superconducting quantum interface device connected thereto.

14. A biomagnetism measuring apparatus as defined in claim 9, further comprising image storage means for storing medical images of a site of interest of said examinee, said field analyzing means being operable to identify said positions of said bioelectric current sources on said medical images by relating said positions of said oscillator coils computed to positions of markers on said medical images.

15. A biomagnetism measuring apparatus as defined in claim 14, further comprising display means for displaying, in superposition, said medical images read from said image storage means, and said positions of said bioelectric current sources identified by said field analyzing means.

16. A biomagnetism measuring apparatus as defined in claim 9, further comprising stimulating means for applying at least one of light, sound and electric stimuli to said examinee.

* * * * *